US009849121B2

(12) United States Patent
Higashiyama

(10) Patent No.: US 9,849,121 B2
(45) Date of Patent: *Dec. 26, 2017

(54) AQUEOUS LIQUID PREPARATIONS AND LIGHT-STABILIZED AQUEOUS LIQUID PREPARATIONS

(71) Applicant: SENJU PHARMACEUTICAL CO., LTD., Osaka (JP)

(72) Inventor: Masayo Higashiyama, Kobe (JP)

(73) Assignee: SENJU PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/511,393

(22) Filed: Oct. 10, 2014

(65) Prior Publication Data

US 2015/0031724 A1    Jan. 29, 2015

Related U.S. Application Data

(60) Continuation of application No. 13/599,212, filed on Aug. 30, 2012, now Pat. No. 8,883,825, which is a division of application No. 10/500,354, filed as application No. PCT/JP03/09713 on Jul. 30, 2003, now Pat. No. 8,784,789.

(30) Foreign Application Priority Data

Jul. 31, 2002 (JP) ................. 2002-223804

(51) Int. Cl.
*A61K 31/4545* (2006.01)
*A61K 47/02* (2006.01)
*A61K 9/00* (2006.01)

(52) U.S. Cl.
CPC ........ *A61K 31/4545* (2013.01); *A61K 9/0043* (2013.01); *A61K 9/0048* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 4,053,628 A | 10/1977 | Stevenson et al. |
| 4,929,618 A | 5/1990 | Koda et al. |
| 5,290,774 A | 3/1994 | Morita et al. |
| 5,294,623 A | 3/1994 | Fukumi et al. |
| 5,599,534 A | 2/1997 | Himmelstein et al. |
| 5,701,182 A | 12/1997 | Hori et al. |
| 5,795,913 A | 8/1998 | Lehmussaari et al. |
| 5,856,345 A | 1/1999 | Doi et al. |
| 5,889,030 A | 3/1999 | Doi et al. |
| 6,174,914 B1 | 1/2001 | Yanni et al. |
| 6,307,052 B1 | 10/2001 | Kita et al. |
| 6,331,540 B1 | 12/2001 | Kabra |
| 6,369,001 B1 | 4/2002 | Jimoh |
| 6,403,609 B1 | 6/2002 | Asgharian |
| 7,175,854 B2 | 2/2007 | Dietrich et al. |
| 2001/0033837 A1 | 10/2001 | Metzner et al. |
| 2002/0026054 A1 | 2/2002 | Kita et al. |
| 2003/0139436 A1 | 7/2003 | Araki et al. |
| 2004/0147605 A1 | 7/2004 | Onuki et al. |

FOREIGN PATENT DOCUMENTS

| | | |
|---|---|---|
| EP | 0 949 260 | 10/1999 |
| EP | 1136084 | 9/2001 |
| EP | 1 277 471 | 1/2003 |
| JP | 404018015 | 1/1992 |
| JP | 11-228404 | 8/1999 |
| JP | 2001-261553 | 9/2001 |
| WO | 98/29409 | 7/1998 |
| WO | 01/002002 | 1/2001 |
| WO | 01/080858 | 11/2001 |
| WO | 2009/142950 | 11/2009 |

OTHER PUBLICATIONS

Tanabe Press Release, "Tanabe Seiyaku Granted Rights for Bepotastine Besilate for Ophthalmic Use to Senju Seiyaku (Japan)", Jul. 17, 2001.*
Remington: The Science and Practice of Pharmacy, 20$^{th}$ ed., pp. 827-828 (2000).*
International Search Report dated Oct. 14, 2003 in International Application No. PCT/JP03/09713.
Derwent Publications, WPI 1999-543925, JP 11228404, Aug. 24, 1999.
Derwent Publications, WPI 2003-880762/200383, JP 2001261553, Sep. 26, 2001.
Remington's Pharmaceutical Sciences, pp. 1410-1419 (1980).
Tropicamide Opthalmic Solution, USP. Package Insert. Revised, Feb. 2000.
The Merck Index, pp. 110-111, 188-189 and 560-561 (2006).
AHF Drug Information, pp. 3558 and 3559 (2001).
Albalon package insert (1996).
Print out from: http://www.paylessonlinepharmacy.com/customer/product-1342-Herplex-D-Idoxuridine-Topical-Solution.html (2010).
Chemical Abstracts, vol. 76(1), p. 24 (1972).
Petition for Inter Partes Review of U.S. Pat. No. 8,784,789 (Feb. 25, 2016).
Petition for Inter Partes Review of U.S. Pat. No. 8,877,168 (Jun. 8, 2016).
Remington: The Science and Practice of Pharmacy 20th Ed. (2000), pp. 729 ,827-832.
Lloyd V. Allen Jr. et al., "Compounding Ophthalmic Preparations," International Journal of Pharmaceutical Compounding, 2(3) (1998).

(Continued)

*Primary Examiner* — Bethany Barham
*Assistant Examiner* — Barbara Frazier
(74) *Attorney, Agent, or Firm* — Wenderoth, Lind & Ponack, L.L.P.

(57) ABSTRACT

An aqueous liquid preparation containing (+)-(S)-4-[4-[(4-chlorophenyl)(2-pyridyl)methoxy]piperidino]butyric acid or a pharmacologically acceptable acid addition salt thereof, which is stabilized with a water-soluble metal chloride, is provided.

11 Claims, No Drawings

(56) References Cited

OTHER PUBLICATIONS

Tetsuya Araki et al., "Photochemical Behavior of Sitafloxacin, Fluoroquinolone Antibiotic, in an Aqueous Solution," Chemical and Pharmaceutical Bulletin, 50(2) 229-234 (2002).

Press Release "Tanabe Seiyaku Granted Rights for Bepotastine Besilate for Ophtalmic Use to Senju Seiyaku (Japan)" (Jul. 17, 2001).

R.J. Davies et al., Antihistamines: topical vs. oral administration, Clinical and Experimental Allergy, 26(3): 11-17 (1996).

"Stability Testing: Photostability Testing of New Drug Substances and Products," ICH Harmonized Tripartite Guideline (1996).

Dolores Kostecka et al., "Formulation of a Stable Parenteral Product; Clonidine Hydrochloride Injection," PDA Journal of Pharmaceutical Science & Technology, 56(6):320-325 (1998).

Gerold L. Mosher et al., "Photoreactivity of LY277359 Maleate, a 5- Hydroxytryptamine$_3$ (5-HT$_3$) Receptor Antagonist, in Solution," Pharmaceutical Research, 8(10): 1215-1222 (1991).

Press Release "Regarding Extended Indication for Selective Histamine H1 Receptor Antagonist/Anti-Allergic Agent Talion® Tablets 5 and Talion® Tablets 10 in Treating Pruritus/Itching Accompanying Urticaria and Other Skin Diseases" (Jan. 25, 2002).

Remington's Pharmaceutical Sciences 16th Ed., pp. 1403-1419 (1980).

\* cited by examiner

AQUEOUS LIQUID PREPARATIONS AND LIGHT-STABILIZED AQUEOUS LIQUID PREPARATIONS

This application is a continuation application of U.S. application Ser. No. 13/599,212, filed Aug. 30, 2012, now U.S. Pat. No. 8,883,825, issued Nov. 11, 2014, which is a divisional application of U.S. application Ser. No. 10/500,354, filed Jun. 30, 2004, now U.S. Pat. No. 8,784,789, issued Jul. 22, 2014, which is the national phase filing of International Patent Application No. PCT/JP2003/009713, filed Jul. 30, 2003.

TECHNICAL FIELD

The present invention relates to an aqueous liquid preparation comprising (+)-(S)-4-[4-[(4-chlorophenyl)(2-pyridyl)methoxy]piperidino]butyric acid or a pharmacologically acceptable acid addition salt thereof, and a water-soluble metal chloride. The present invention also relates to a method of light-stabilizing (+)-(S)-4-[4-[(4-chlorophenyl)(2-pyridyl)methoxy]piperidino]butyric acid and a pharmacologically acceptable acid addition salt thereof, which comprises adding a water-soluble metal chloride.

BACKGROUND ART (+)-(S)-4-[4-[(4-Chlorophenyl)(2-pyridyl)methoxy]piperidino]butyric acid and a pharmacologically acceptable acid addition salt thereof have an antihistaminic action and an antiallergic action. They are also characterized in that secondary effects such as stimulation or suppression of the central nerve often seen in the case of conventional antihistaminic agents can be minimized, and can be used as effective pharmaceutical agents for the treatment of human and animals (JP-B-5-33953, JP-A-2000-198784).

Particularly, a tablet comprising (+)-(S)-4-[4-[(4-chlorophenyl)(2-pyridyl)methoxy]piperidino]butyric acid monobenzenesulfonate (general name: bepotastine besilate) has been already marketed as a therapeutic agent for allergic rhinitis and itching associated with hives and dermatoses.

On the other hand, (+)-(S)-4-[4-[(4-chlorophenyl)(2-pyridyl)methoxy]piperidino]butyric acid and a pharmacologically acceptable acid addition salt thereof are unstable to light in an aqueous solution, and colored or precipitated with the lapse of time, which has made the use thereof as an aqueous liquid preparation difficult. In the case of an aqueous liquid preparation such as an eye drop and a nasal drop, a method comprising blocking light by preserving in a light-shielding container and the like can be used, but complete light-shielding is practically difficult. Thus, stabilization of an aqueous liquid preparation itself as a preparation is desirable. As a method of light-stabilizing an eye drop, a U.S. Pat. No. 2,929,274 discloses a method comprising adding boric acid and/or borax and glycerin, but according to this method, stabilization of (+)-(S)-4-[4-[(4-chlorophenyl)(2-pyridyl)methoxy]piperidino]butyric acid and a pharmacologically acceptable acid addition salt thereof to light was not observed. As a general stabilization method, a method comprising placing in the coexistence of an antioxidant such as BHT etc., and the like are known (JP-A-7-304670).

DISCLOSURE OF THE INVENTION

The present invention aims at providing an aqueous liquid preparation comprising stabilized (+)-(S)-4-[4-[(4-chlorophenyl)(2-pyridyl)methoxy]piperidino]butyric acid or a pharmacologically acceptable acid addition salt thereof.

Another object of the present invention is to provide a method of light-stabilizing (+)-(S)-4-[4-[(4-chlorophenyl)(2-pyridyl)methoxy]piperidino]butyric acid and a pharmacologically acceptable acid addition salt thereof in an aqueous solution.

Under the above-mentioned situation, the present inventor has conducted various studies and, as a result, found that (+)-(S)-4-[4-[(4-chlorophenyl)(2-pyridyl)methoxy]piperidino]butyric acid and a pharmacologically acceptable acid addition salt thereof can be light-stabilized in water by adding a water-soluble metal chloride, and further studied to complete the present invention.

Accordingly, the present invention relates to (1) an aqueous liquid preparation comprising (+)-(S)-4-[4-[(4-chlorophenyl)(2-pyridyl)methoxy]piperidino]butyric acid or a pharmacologically acceptable acid addition salt thereof, and a water-soluble metal chloride, (2) the aqueous liquid preparation of the above-mentioned (1), wherein the metal chloride has a concentration selected from the range of a lower limit concentration of 0.15 w/v % and an upper limit concentration of 1.5 w/v %, (3) the aqueous liquid preparation of the above-mentioned (1) or (2), wherein the metal chloride is at least one kind selected from sodium chloride, potassium chloride and calcium chloride, (4) the aqueous liquid preparation of any of the above-mentioned (1) to (3), wherein the (+)-(S)-4-[4-[(4-chlorophenyl)(2-pyridyl)methoxy]piperidino]butyric acid or the pharmacologically acceptable acid addition salt thereof has a concentration selected from the range of a lower limit concentration of 0.1 w/v % and an upper limit concentration of 2.0 w/v %, (5) the aqueous liquid preparation of any of the above-mentioned (1) to (4), which is an acid addition salt of (+)-(S)-4-[4-[(4-chlorophenyl)(2-pyridyl) methoxy]piperidino]butyric acid, (6) the aqueous liquid preparation of the above-mentioned (5), wherein the acid addition salt is monobenzenesulfonate, (7) the aqueous liquid preparation of any of the above-mentioned (1) to (6), wherein the aqueous liquid preparation has a pH in the range of 4-8.5, (8) the aqueous liquid preparation of any of the above-mentioned (1) to (7), which is an eye drop, (9) the aqueous liquid preparation of any of the above-mentioned (1) to (7), which is a nasal drop,

(10) an aqueous eye drop comprising (+)-(S)-4-[4-[(4-chlorophenyl)(2-pyridyl)methoxy]piperidino]butyric acid monobenzenesulfonate and sodium chloride at not less than 0.2 w/v % and not more than 0.8 w/v %, and

(11) a method of light-stabilizing (+)-(S)-4-[4-[(4-chlorophenyl)(2-pyridyl)methoxy]piperidino]butyric acid in an aqueous solution, which comprises adding a water-soluble metal chloride to an aqueous solution comprising (+)-(S)-4-[4-[(4-chlorophenyl) (2-pyridyl)methoxy]piperidino]butyric acid or a pharmacologically acceptable acid addition salt thereof.

In the present invention, as a pharmacologically acceptable acid addition salt of (+)-(S)-4-[4-[(4-chlorophenyl)(2-pyridyl)methoxy]piperidino]butyric acid, for example, salts with hydrohalic acid such as hydrochloride, hydrobromide and the like; salts with inorganic acid such as sulfate, nitrate, phosphate and the like; salts with organic acid such as acetate, propionate, hydroxyacetate, 2-hydroxypropionate, pyruvate, malonate, succinate, maleate, fumarate, dihydroxyfumarate, oxalate, benzoate, cinnamate, salicylate, methanesulfonate, ethanesulfonate, benzenesulfonate, p-toluenesulfonate, cyclohexylsulfamate, 4-aminosalicylate and the like; and the like can be mentioned. The above-mentioned compound to be used in the present invention is generally preferably an acid addition salt, and of these acid addition salts, benzenesulfonate and benzoate are more preferable, and monobenzenesulfonate is particularly preferable.

(+)-(S)-4-[4-[(4-Chlorophenyl) (2-pyridyl)methoxy]piperidino]butyric acid and a pharmacologically acceptable acid addition salt thereof can be produced by, for example, the methods described in JP-B-5-33953 and JP-A-2000-198784.

In the aqueous liquid preparation of the present invention, the content of (+)-(S)-4-[4-[(4-chlorophenyl) (2-pyridyl)methoxy]piperidino]butyric acid or a pharmacologically acceptable salt thereof as monobenzenesulfonate is generally shown by a lower limit of about 0.1 w/v %, preferably about 0.3 w/v %, more preferably about 0.5 w/v %, and an upper limit of about 2.0 w/v %, preferably about 1.5 w/v %, which are increased or decreased appropriately depending on the object of use and the degree of symptoms.

In the present invention, as a preferable water-soluble metal chloride, alkali metal chlorides such as sodium chloride, potassium chloride and the like, and alkaline earth metal chlorides such as calcium chloride and the like can be mentioned, which may be used alone, or in combination of two or more kinds thereof. Particularly preferred is sodium chloride.

In the aqueous liquid preparation of the present invention, the content of the water-soluble metal chloride is generally shown by a lower limit of about 0.15 w/v % and an upper limit of about 1.5 w/v %, preferably a lower limit of about 0.2 w/v % and an upper limit of about 1.2 w/v %. Particularly, as sodium chloride, it is not less than about 0.15 w/v %, about 0.2 w/v %, about 0.3 w/v %, and not more than about 1.0 w/v %, about 0.8 w/v %, about 0.6 w/v %. As potassium chloride, it is not less than about 0.15 w/v %, about 0.2 w/v %, about 0.3 w/v %, and not more than about 1.0 w/v %, about 0.9 w/v %, about 0.8 w/v %. As calcium chloride and as dihydrate, it is not less than about 0.2 w/v %, about 0.3 w/v %, and not more than about 1.5 w/v %, about 1.2 w/v %.

Moreover, the concentration of these water-soluble metal chlorides is preferably determined as appropriate within the above-mentioned concentration range, such that the osmotic pressure is generally about 230 mOsm-about 350 mOsm, in consideration of the amount of other isotonic agents to be added, such as boric acid and the like, that do not influence stabilization.

Various additives that are generally used such as buffer, preservative, chelating agent, flavor and the like may be appropriately added to the aqueous liquid preparation of the present invention.

As the buffer, for example, phosphate buffer, borate buffer, citrate buffer, tartrate buffer, acetate buffer, amino acid and the like can be mentioned. As the preservative, for example, quaternary ammonium salts such as benzalkonium chloride, chlorhexidine gluconate and the like, parahydroxybenzoic acid esters such as methyl parahydroxybenzoate, propyl parahydroxybenzoate and the like, sorbic acid and a salt thereof and the like can be mentioned. As the chelating agent, disodium edetate, citric acid and the like can be mentioned. As the flavor, l-menthol, borneol, camphor, oil of eucalyptus and the like can be mentioned.

The pH of the aqueous liquid preparation of the present invention is adjusted to not less than about 4, 5, 6, and not more than about 8.5, 8.

In the aqueous liquid preparation of the present invention, other same or different kinds of efficacious ingredients may be added appropriately as long as the object of the present invention is not impaired.

As the aqueous liquid preparation of the present invention, an eye drop, a nasal drop, an ear drop and the like can be mentioned. When the aqueous liquid preparation of the present invention is used as a nasal drop, it may be prepared into a propellant.

The aqueous liquid preparation of the present invention can be produced by a production method known per se, such as a method described in the liquid preparation or eye drop of the General Rules for Preparations in the Japanese Pharmacopoeia 14th Edition.

The aqueous liquid preparation of the present invention can be used for warm-blooded animals (e.g., human, rat, mouse, rabbit, bovine, pig, dog, cat and the like).

When the aqueous liquid preparation of the present invention is used as, for example, an eye drop, it can be used for allergic conjunctivitis, spring catarrh, pollinosis and the like. The dose thereof when, for example, an eye drop of the present invention comprising 1.0 w/v % of (+)-(S)-4-[4-[(4-chlorophenyl)(2-pyridyl)methoxy]piperidino]butyric acid monobenzenesulfonate (hereinafter to be referred to as bepotastine besilate) is instilled into the eye of an adult, is 1-2 drops per instillation, which is given 3-6 times a day by instillation into the eye. The frequency can be increased or decreased appropriately depending on the degree of symptom.

BEST MODE FOR EMBODYING THE INVENTION

The present invention is explained in more detail by referring to Experimental Examples and Examples, which are not to be construed as limitative.

Experimental Example 1 Effect of Water-Soluble Metal Chloride on Light-Stability of Bepotastine Besilate Test Method The aqueous liquid preparations (Formulations 1-6) shown in the following [Table 1], which contained bepotastine besilate, were prepared according to conventional methods and filled in glass ampoules by 5 mL each. Using a xenon long-life fade meter (FAL-25AX-Ec manufactured by SUGA TEST INSTRUMENTS Co., Ltd.), a light corresponding to not less than 200 W·h/m$^2$ in a total near-ultraviolet radiation energy was irradiated (irradiation time: 23-34 hr), and appearance of each formulated liquid preparation was observed. The amount of light exposure was measured by a quinine chemical actinometry system described in the Drug Approval and Licensing Procedures in Japan 2001.

TABLE 1

| | Formulation | | | | | |
|---|---|---|---|---|---|---|
| | 1 | 2 | 3 | 4 | 5 | 6 |
| bepotastine besilate | 1.5 g | 1.5 g | 1.5 g | 1.5 g | 1.5 g | 1.5 g |

TABLE 1-continued

| | Formulation | | | | | |
|---|---|---|---|---|---|---|
| | 1 | 2 | 3 | 4 | 5 | 6 |
| sodium chloride | — | 0.1 g | 0.2 g | 0.3 g | — | — |
| potassium chloride | — | — | — | — | 0.79 g | — |
| calcium chloride 2H$_2$O | — | — | — | — | — | 1.18 g |
| sodium hydroxide | suitable amount | suitable amount | suitable amount | suitable amount | suitable amount | suitable amount |
| total amount | 100 mL | 100 mL | 100 mL | 100 mL | 100 mL | 100 mL |
| PH | 7.0 | 7.0 | 6.7 | 6.9 | 6.7 | 6.8 |

Test Results

The appearance after light irradiation was black green in Formulation 1, and a precipitate was observed. It was slightly dark green-pale yellow in Formulation 2, and a precipitate was slightly observed. The appearance of Formulations 3-6 did not change from that immediately after preparation and were pale yellow and clear. The results indicate that addition of a water-soluble metal chloride in not less than 0.2 w/v % improves stability of bepotastine besilate under light irradiation conditions.

Experimental Example 2 Effect of Boric Acid and Glycerin on Light-Stability of Bepotastine Besilate Test Method The aqueous liquid preparations (Formulations 7-9) shown in the following [Table 2], which contained bepotastine besilate, were prepared according to conventional methods and processed in the same manner as in Experimental Example 1, and appearance of each formulated liquid preparation was observed.

TABLE 2

| Formulation | 7 | 8 | 9 |
|---|---|---|---|
| bepotastine besilate | 1.5 g | 1.5 g | 1.5 g |
| sodium dihydrogen phosphate dihydrate | 0.1 g | — | — |
| boric acid | — | 1.0 g | 0.5 g |
| sodium chloride | 0.6 g | — | — |
| glycerin | — | 0.5 g | 2.0 g |
| benzalkonium chloride | 0.005 g | 0.005 g | 0.005 g |
| sodium hydroxide | suitable amount | suitable amount | suitable amount |
| total amount | 100 mL | 100 mL | 100 mL |
| pH | 6.8 | 6.8 | 6.8 |

Test Results

The appearance after light irradiation did not change from that immediately after preparation and was pale yellow and clear for Formulation 7 comprising sodium chloride, but black green for Formulations 8 and 9 comprising boric acid and glycerin and a precipitate was observed. The results indicate that addition of boric acid and glycerin fails to improve stability of bepotastine besilate under light irradiation conditions.

Experimental Example 3 Effect of pH and Bepotastine Besilate Concentration on Light-Stability of Bepotastine Besilate Test Method The aqueous liquid preparations (Formulations 10-12) shown in the following [Table 3], which contained bepotastine besilate, were prepared according to conventional methods and processed in the same manner as in Experimental Example 1, and appearance of each formulated liquid preparation was observed.

TABLE 3

| Formulation | 10 | 11 | 12 |
|---|---|---|---|
| bepotastine besilate | 1.5 g | 1.5 g | 0.1 g |
| sodium dihydrogen phosphate dihydrate | 0.1 g | 0.1 g | 0.1 g |
| sodium chloride | 0.6 g | 0.6 g | 0.82 g |
| benzalkonium chloride | 0.005 g | 0.005 g | 0.005 g |
| sodium hydroxide | suitable amount | suitable amount | suitable amount |
| total amount | 100 mL | 100 mL | 100 mL |
| pH | 4.0 | 8.5 | 6.8 |

Test Results

The appearance after light irradiation did not change from that immediately after preparation and was pale yellow and clear for Formulation 10 (pH 4) and Formulation 11 (pH 8.5) comprising sodium chloride. In addition, the appearance did not change from that immediately after preparation and was colorless and clear for Formulation 12 having a bepotastine besilate concentration of 0.1 w/v %. These results and the results of Formulation 7 (pH 6.8) in Experimental Example 2 indicate that addition of sodium chloride, which is a water-soluble metal chloride, improves light stability of bepotastine besilate at pH 4-8.5. In addition, they indicate that the light-stability of bepotastine besilate is improved in the concentration range of 0.1 w/v %-1.5 w/v %.

Experimental Example 4 Effect of Bepotastine Besilate Concentration and pH on Light-Stability of Bepotastine Besilate in Aqueous Preparation Comprising Glycerin Test Method The aqueous liquid preparations (Formulations 13-17) shown in the following [Table 4], which contained bepotastine besilate, were prepared according to conventional methods and processed in the same manner as in Experimental Example 1, and appearance of each formulated liquid preparation was observed.

TABLE 4

| Formulation | 13 | 14 | 15 | 16 | 17 |
|---|---|---|---|---|---|
| bepotastine besilate | 0.5 g | 1.0 g | 1.5 g | 1.5 g | 1.5 g |
| sodium dihydrogen phosphate dihydrate | 0.1 g | 0.1 g | 0.1 g | 0.1 g | 0.1 g |

TABLE 4-continued

| Formulation | 13 | 14 | 15 | 16 | 17 |
|---|---|---|---|---|---|
| glycerin | 2.2 g | 2.0 g | 1.7 g | 1.7 g | 1.7 g |
| benzalkonium chloride | 0.005 g | 0.005 g | 0.005 g | 0.005 g | 0.005 g |
| sodium hydroxide | suitable amount | suitable amount | suitable amount | suitable amount | suitable amount |
| total amount | 100 mL | 100 mL | 100 mL | 100 mL | 100 mL |
| pH | 6.8 | 6.8 | 4.0 | 6.8 | 8.5 |

Test Results

The appearance after light irradiation was pale black green for Formulation 13 and black green for Formulation 14, and a precipitate was observed in both Formulations. The results indicate that addition of glycerin results in coloration of bepotastine besilate into black green even at a low concentration.

Formulation 15 (pH 4) turned blue and a precipitate was observed. Formulation 16 (pH 6.8) turned black green and a precipitate was observed. Formulation 17 (pH 8.5) turned yellow brown but no precipitation was observed. The results indicate that bepotastine besilate is extremely unstable at a pH near neutral. The results also indicate that glycerin does not improve light-stability of bepotastine besilate in the range of pH 4-8.5. When 3.3 w/v % of glucose or mannitol was added instead of glycerin of Formulation 16, black green was developed and a precipitate was observed. These results indicate that a water-soluble metal chloride improves light-stability of bepotastine besilate, and isotonic agents such as glycerin, saccharides and the like do not improve light-stability of bepotastine besilate.

Example 1: Eye Drop

| | |
|---|---|
| bepotastine besilate | 0.3 g |
| Sodium dihydrogenphosphate dihydrate | 0.1 g |
| sodium chloride | 0.79 g |
| benzalkonium chloride | 0.005 g |
| sodium hydroxide | suitable amount |
| sterile purified water total amount | 100 mL |
| | pH 6.8 |

Using the above-mentioned ingredients, an eye drop is prepared by a conventional method.

Example 2 Eye Drop

| | |
|---|---|
| bepotastine besilate | 0.5 g |
| Sodium dihydrogenphosphate dihydrate | 0.1 g |
| sodium chloride | 0.76 g |
| benzalkonium chloride | 0.005 g |
| sodium hydroxide | suitable amount |
| sterile purified water total amount | 100 mL |
| | pH 6.8 |

Using the above-mentioned ingredients, an eye drop is prepared by a conventional method Example 3 Eye Drop

| | |
|---|---|
| bepotastine besilate | 1.0 g |
| Sodium dihydrogenphosphate dihydrate | 0.1 g |
| sodium chloride | 0.68 g |
| benzalkonium chloride | 0.005 g |
| sodium hydroxide | suitable amount |
| sterile purified water total amount | 100 mL |
| | pH 6.8 |

Using the above-mentioned ingredients, an eye drop is prepared by a conventional method Example 4 Eye Drop

| | |
|---|---|
| bepotastine besilate | 1.5 g |
| Sodium acetate trihydrate | 0.1 g |
| sodium chloride | 0.6 g |
| benzalkonium chloride | 0.005 g |
| sodium hydroxide | suitable amount |
| sterile purified water total amount | 100 mL |
| | pH 4.0 |

Using the above-mentioned ingredients, an eye drop is prepared by a conventional method.

Example 5 Eye Drop

| | |
|---|---|
| bepotastine besilate | 1.5 g |
| epsilon-aminocaproic acid | 0.1 g |
| sodium chloride | 0.6 g |
| benzalkonium chloride | 0.005 g |
| sodium hydroxide | suitable amount |
| sterile purified water total amount | 100 mL |
| | pH 4.0 |

Using the above-mentioned ingredients, an eye drop is prepared by a conventional method.

Example 6 Eye Drop

| | |
|---|---|
| bepotastine besilate | 1.5 g |
| citric acid | 0.1 g |
| sodium chloride | 0.6 g |
| benzalkonium chloride | 0.005 g |
| sodium hydroxide | suitable amount |
| sterile purified water total amount | 100 mL |
| | pH 6.8 |

Using the above-mentioned ingredients, an eye drop is prepared by a conventional method.

Example 7 Eye Drop

| | |
|---|---|
| bepotastine besilate | 1.5 g |
| taurine | 0.1 g |

|  |  |
|---|---|
| sodium chloride | 0.6 g |
| benzalkonium chloride | 0.005 g |
| sodium hydroxide | suitable amount |
| sterile purified water total amount | 100 mL |
|  | pH 8.5 |

Using the above-mentioned ingredients, an eye drop is prepared by a conventional method.

Example 8 Eye Drop

|  |  |
|---|---|
| bepotastine besilate | 1.5 g |
| sodium dihydrogenphosphate dihydrate | 0.1 g |
| sodium chloride | 0.6 g |
| methyl parahydroxybenzoate | 0.026 g |
| propyl parahydroxybenzoate | 0.014 g |
| sodium hydroxide | suitable amount |
| sterile purified water total amount | 100 mL |
|  | pH 6.8 |

Using the above-mentioned ingredients, an eye drop is prepared by a conventional method.

Example 9 Eye Drop

|  |  |
|---|---|
| bepotastine besilate | 1.5 g |
| sodium dihydrogenphosphate dihydrate | 0.1 g |
| sodium chloride | 0.6 g |
| potassium sorbate | 0.27 g |
| sodium hydroxide | suitable amount |
| sterile purified water total amount | 100 mL |
|  | pH 6.8 |

Using the above-mentioned ingredients, an eye drop is prepared by a conventional method.

Example 10 Eye Drop

|  |  |
|---|---|
| bepotastine besilate | 1.5 g |
| sodium dihydrogenphosphate dihydrate | 0.1 g |
| sodium chloride | 0.6 g |
| chlorhexidine gluconate | 0.005 g |
| sodium hydroxide | suitable amount |
| sterile purified water total amount | 100 mL |
|  | pH 6.8 |

Using the above-mentioned ingredients, an eye drop is prepared by a conventional method.

Example 11 Eye Drop

|  |  |
|---|---|
| bepotastine besilate | 1.5 g |
| sodium dihydrogenphosphate dihydrate | 0.1 g |
| sodium chloride | 0.6 g |
| benzalkonium chloride | 0.005 g |
| sodium hydroxide | suitable amount |
| sterile purified water total amount | 100 mL |
|  | pH 6.8 |

Using the above-mentioned ingredients, an eye drop is prepared by a conventional method.

Example 12 Nasal Drop

|  |  |
|---|---|
| bepotastine besilate | 1.0 g |
| sodium dihydrogenphosphate dihydrate | 0.1 g |
| sodium chloride | 0.68 g |
| benzalkonium chloride | 0.005 g |
| sodium hydroxide | suitable amount |
| sterile purified water total amount | 100 mL |
|  | pH 6.8 |

Using the above-mentioned ingredients, a nasal drop is prepared by a conventional method.

INDUSTRIAL APPLICABILITY

In the present invention, the light-stability of (+)-(S)-4-[4-[(4-chlorophenyl)(2-pyridyl)methoxy]piperidino]butyric acid or a pharmacologically acceptable acid addition salt thereof, particularly bepotastine besilate, which is monobenzenesulfonate, can be improved by adding a water-soluble metal chloride to an aqueous liquid preparation comprising (+)-(S)-4-[4-[(4-chlorophenyl)(2-pyridyl)methoxy]piperidino]butyric acid or a pharmacologically acceptable acid addition salt thereof, and a stable aqueous liquid preparation can be produced. Since an aqueous liquid preparation stable to light can be obtained by the light-stabilizing method of the present invention, the aqueous liquid preparation of the present invention is advantageously used for the treatment of allergic conjunctivitis, spring catarrh, pollinosis, allergic rhinitis and the like.

While some of the embodiments of this invention have been described in detail in the foregoing, it will be possible for those of ordinary skill in the art to variously modify and change the embodiments specifically shown herein, within the scope not substantially deviating from the novel teaching and benefit of the invention. Accordingly, this invention encompasses all such modifications and changes within the spirit and scope of the invention as defined by the following claims.

This application is based on a patent application No. 223804/2002 filed in Japan, the contents of which are hereby incorporated by reference.

The invention claimed is:

1. An aqueous liquid preparation consisting essentially of (+)-(S)-4-[4-[(4-chlorophenyl)(2-pyridyl)methoxy]piperidino]butyric acid or a pharmacologically acceptable acid addition salt thereof as a sole therapeutic agent, and a water-soluble metal chloride in an amount sufficient to prevent precipitation of the sole therapeutic agent in the aqueous liquid preparation upon exposure to light, wherein the metal chloride has a concentration selected from the range of a lower limit concentration of 0.15 w/v % and an upper limit concentration of 1.5 w/v %, and wherein the aqueous liquid preparation has a pH in the range of 8.1-8.5.

2. The aqueous liquid preparation of claim 1, wherein the metal chloride is at least one kind selected from sodium chloride, potassium chloride and calcium chloride.

3. The aqueous liquid preparation of claim 1, wherein the (+)-(S)-4-[4-[(4-chlorophenyl)(2-pyridyl)methoxy]piperidino]butyric acid or the pharmacologically acceptable acid addition salt thereof as the sole therapeutic agent has a concentration selected from the range of a lower limit concentration of 0.1 w/v % and an upper limit concentration of 2.0 w/v %.

4. The aqueous liquid preparation of claim 1, wherein the sole therapeutic agent is an acid addition salt of (+)-(S)-4-[4-[(4-chlorophenyl)(2-pyridyl)methoxy]piperidino]butyric acid.

5. The aqueous liquid preparation of claim 4, wherein the acid addition salt is monobenzenesulfonate.

6. The aqueous liquid preparation of claim 1, which is an eye drop.

7. The aqueous liquid preparation of claim 1, which is a nasal drop.

8. An aqueous eye drop consisting essentially of (+)-(S)-4-[4-[(4-chlorophenyl)(2-pyridyl)methoxy]piperidino]butyric acid monobenzenesulfonate as a sole therapeutic agent, and sodium chloride at not less than 0.2 w/v % and not more than 0.8 w/v %, wherein the sodium chloride prevents precipitation of the sole therapeutic agent in the eye drop upon exposure to light, and wherein the eye drop has a pH in the range of 8.1-8.5.

9. A method of light-stabilizing (+)-(S)-4-[4-[(4-chlorophenyl)(2-pyridyl)methoxy]piperidino]butyric acid or a pharmacologically acceptable acid addition salt thereof as a sole therapeutic agent in an aqueous solution, the method comprising:

adding a water-soluble metal chloride to an aqueous solution consisting essentially of the (+)-(S)-4-[4-[(4-chlorophenyl)(2-pyridyl)methoxy]piperidino]butyric acid or the pharmacologically acceptable acid addition salt thereof as the sole therapeutic agent in an amount sufficient to prevent precipitation of the sole therapeutic agent upon exposure to light, wherein the metal chloride has a concentration selected from the range of a lower limit concentration of 0.15 w/v % and an upper limit concentration of 1.5 w/v %, and wherein the aqueous solution has a pH in the range of 8.1-8.5.

10. The method of claim 9, wherein the (+)-(S)-4-[4-[(4-chlorophenyl)(2-pyridyl)methoxy]piperidino]butyric acid or the pharmacologically acceptable acid addition salt thereof as the sole active ingredient has a concentration selected from the range of a lower limit concentration of 0.1 w/v % and an upper limit concentration of 2.0 w/v %.

11. An aqueous eye drop consisting essentially of:

a therapeutic agent consisting of (+)-(S)-4-[4-[(4-chlorophenyl)(2-pyridyl)methoxy]piperidino]butyric acid monobenzenesulfonate, and sodium chloride at not less than 0.2 w/v % and not more than 0.8 w/v %, wherein the sodium chloride prevents precipitation of the therapeutic agent in the eye drop upon exposure to light, and wherein the eye drop has a pH in the range of 8.1-8.5.

* * * * *